(12) United States Patent
Virta

(10) Patent No.: US 8,500,642 B2
(45) Date of Patent: Aug. 6, 2013

(54) ULTRASONIC TREATMENT APPARATUS WITH A PROTECTIVE COVER

(75) Inventor: Tero Jouko Valtter Virta, Espoo (FI)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 13/063,767

(22) PCT Filed: Sep. 11, 2009

(86) PCT No.: PCT/IB2009/053987
§ 371 (c)(1),
(2), (4) Date: Mar. 14, 2011

(87) PCT Pub. No.: WO2010/032186
PCT Pub. Date: Mar. 25, 2010

(65) Prior Publication Data
US 2011/0166484 A1    Jul. 7, 2011

(30) Foreign Application Priority Data

Sep. 18, 2008    (EP) .................................. 08164551

(51) Int. Cl.
*A61B 8/00*    (2006.01)
(52) U.S. Cl.
USPC .......................................... 600/439; 600/459

(58) Field of Classification Search
USPC .................................. 600/437–469; 601/1–3
See application file for complete search history.

(56) References Cited

U.S. PATENT DOCUMENTS

| | | | |
|---|---|---|---|
| 5,072,723 A | 12/1991 | Viebach | |
| 5,275,165 A | 1/1994 | Ettinger et al. | |
| 5,443,068 A | 8/1995 | Cline et al. | |
| 5,590,653 A * | 1/1997 | Aida et al. | 600/411 |
| 7,789,841 B2 * | 9/2010 | Huckle et al. | 601/2 |
| 8,123,707 B2 * | 2/2012 | Huckle et al. | 601/2 |
| 2002/0188229 A1 * | 12/2002 | Ryaby et al. | 601/2 |
| 2003/0153849 A1 * | 8/2003 | Huckle et al. | 601/2 |
| 2004/0103477 A1 | 6/2004 | Gagnon et al. | |
| 2005/0080333 A1 | 4/2005 | Piron et al. | |
| 2005/0154308 A1 | 7/2005 | Quistgaard et al. | |

FOREIGN PATENT DOCUMENTS

| | | |
|---|---|---|
| EP | 1854508 | 11/2007 |
| EP | 1913974 | 4/2008 |

* cited by examiner

*Primary Examiner* — Sanjay Cattungal

(57) ABSTRACT

An ultrasonic treatment apparatus comprised of: a patient support for supporting a patient, an ultrasound transducer system for ultrasonic treatment of the patient, a region formed in the patient support operable for transmitting ultrasound from the ultrasound transducer system to a treatment zone in the patient, a protective cover for covering the region, and wherein the protective cover is adapted to be removed from the region while the patient is positioned relative to the treatment zone such that the treatment zone is able to receive treatment from the ultrasound transducer system.

16 Claims, 8 Drawing Sheets

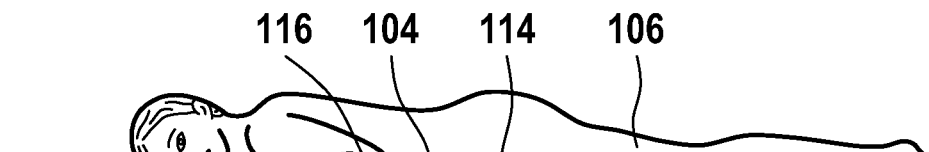
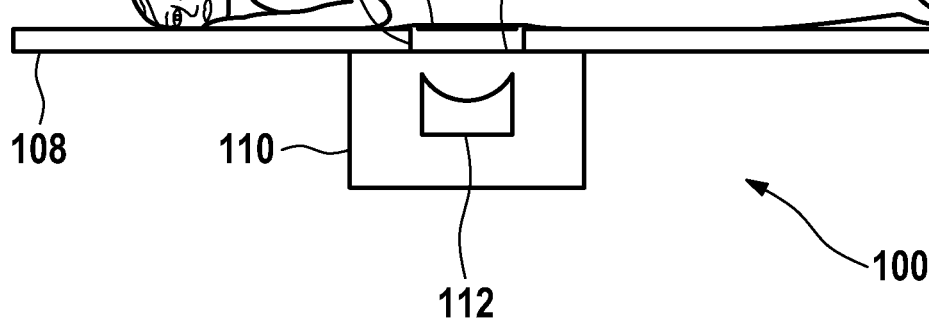
FIG. 1

ULTRASONIC TREATMENT APPARATUS WITH A PROTECTIVE COVER

FIELD OF THE INVENTION

The present invention relates to an ultrasonic treatment apparatus and a cartridge comprised of an ultrasonic coupling and a protective cover.

BACKGROUND OF THE INVENTION

Ultrasound from a focused ultrasonic transducer can be used to selectively treat regions within the interior of the body. Ultrasonic waves are transmitted as high energy mechanical vibrations. These vibrations induce tissue heating as they are damped, and they can also lead to cavitation. Both tissue heating and cavitation can be used to destroy tissue in a clinical setting. However, heating tissue with ultrasound is easier to control than cavitation. Ultrasonic treatments can be used to ablate tissue and to kill regions of cancer cells selectively. This technique has been applied to the treatment of uterine fibroids, and has reduces the need for hysterectomy procedures.

To selectively treat tissue, a focused ultrasonic transducer can be used to focus the ultra sound on a particular treatment volume. The transducer is typically mounted within a medium, such as degassed water, that is able to transmit ultrasound. Actuators are then used to adjust the position of the ultrasonic transducer and thereby adjust the tissue region that is being treated. U.S. Pat. No. 5,590,653 describes a medical treatment apparatus where the position of an ultrasonic transducer is adjustable and is integrated into a patient table.

Standard medical imaging techniques are commonly used to plan the ultrasound treatment and can also be used to guide the treatment. Magnetic Resonance Imaging (MRI), Computed Tomography y (CT), and ultrasonic imaging have been used for the planning and guiding of ultrasonic treatments. Focused ultrasonic transducers typically have a limited range over which they can be actuated, so the patient must be positioned properly relative to the ultrasonic treatment apparatus. Ultrasound is not able to be transmitted to the body through air, so an ultrasound coupling such as ultrasonic gel, an ultrasonic gel pad, or degassed water is used to transmit the ultrasound from the ultrasonic treatment apparatus to the skin of the patient. Typically a membrane such as Mylar is used to form a boundary between the ultrasonic treatment apparatus and the medium used to conduct ultrasound to the patient.

A problem with current ultrasonic treatment apparatuses is that the Mylar membranes are fragile and that the ultrasound coupling may not form a good path for the ultrasound if the patient is positioned on the coupling more than once. For many treatment procedures, the patient is positioned relative to the treatment apparatus and a medical imaging technique is used to check the orientation of the patient's anatomy relative to the ultrasonic transducer. If the patient is not orientated relative to the ultrasonic transducer properly, he or she will need to be repositioned. This can cause the ultrasound coupling to be damaged. In this case the coupling will need to be replaced, and this typically means that the process of orientating the patient relative to the ultrasonic transducer needs to be started again. Additionally when the patient is positioning himself or herself on the ultrasonic treatment apparatus, the Mylar window can be damaged, or the ultrasonic coupling disturbed.

SUMMARY OF THE INVENTION

The invention provides for an ultrasonic treatment apparatus and a cartridge as claimed in the independent claims. Embodiments of the invention are given in the dependent claims.

Embodiments of the invention address the aforementioned problems by protecting the region that transmits ultrasound to the patient with a protective cover. This protects ultrasound gel pad or other ultrasound coupling during the patient setup, positioning and possible test images. This also protects any ultrasound membrane, such as Mylar, when the patient is stepping onto or off of the table or patent support. An ultrasound membrane is defined to be a thin membrane which is adapted for the transmission of ultrasound. The cover can also be used to protect the ultrasound membrane when the ultrasonic treatment apparatus is not in use.

Embodiments of the invention provide for an ultrasonic treatment apparatus comprised of a patient support that is able to support a patient, an ultrasonic transducer that is used for the ultrasonic treatment of patients, a region which is formed in the patient support for transmitting ultrasound from the ultrasound transducer system to a treatment zone on the patient, and a protective cover for covering the region. The treatment zone is defined to be the region of the patient which is being treated by the ultrasonic treatment apparatus.

The protective cover is able to be removed from the region when the patient is positioned relative to the treatment zone such that the treatment zone is able to receive treatment from the ultrasound transistor system. This has the advantage that typically an ultrasonic coupling agent such as an ultrasonic gel or an ultrasonic gel pad is used to couple the ultrasound from the transducer system to the skin of the patient. The patient is able to position him or herself properly on the patient support when the protective cover is in place without causing the ultrasound coupling agent to be disturbed. When the patient is in the correct position, then the protective cover can be removed from the region. This is more pleasant for the patient than having to repeatedly be repositioned and replacing the ultrasonic coupling material, and it also increases the workflow and allows examinations or treatments to proceed more rapidly.

In another embodiment the patient support has a surface which slopes towards the region which transmits the ultrasound. This sloped region supports the patient and serves to partially support the patient so that when the protective cover is removed there is less weight from the patient on the protective cover. This has the advantage that it is easier to remove the protective cover and it is more comfortable for the patient. The sloped surface is also more comfortable for the patient and aids in properly positioning the patient.

In another embodiment the ultrasonic treatment apparatus indicates a medical imaging device. The advantage of incorporating the medical imaging device is that the medical imaging device can be used for guiding the ultrasonic treatment. This allows physicians to precisely locate and treat regions within the body of the patient. The medical imaging device for this type of procedure is comprised of an MRI scanner, a CT scanner or an ultrasound imaging system. The advantage of this is that these imaging techniques are all compatible with the ultrasound treatment and are able to image the tumors during the ultrasound treatment.

Guiding the ultrasonic treatment is herein defined as meaning using a medical image device before or during or after an ultrasonic treatment to properly locate and treat a volume within a patient. This can be implemented in different ways. The entire treatment apparatus can be within the volume that is able to be imaged using a medical imaging device during the guiding process. Another alternative is that ultrasonic transducer and imaging device are in separate locations. The patient can be moved with a movable patient support between the imaging apparatus and the ultrasonic transducer.

In another embodiment there is an ultrasound membrane which is adapted for transmitting ultrasound which separates the ultrasound transducer system from an ultrasound coupling. The ultrasound coupling is adapted to transmit ultrasound from the ultrasound membrane to the dermis of a patient. This has the advantage that the ultrasound membrane separates the acoustic or ultrasound coupling material from the ultrasound transducer system. Materials used for ultrasound coupling are typically liquid or gel like and the membrane protects the ultrasonic transistor system from the ultrasound coupling material.

In another embodiment the protective cover is slideably engaged. This is very advantageous, because the patient can be resting against the protective cover and the protective cover can simply be slid away. By sliding the cover away the patient does not need to be moved or be repositioned.

In another embodiment the protective cover is comprised of two slideably engaged plates. As in the previous embodiment this has the advantage that the patient can remain in place when the protective cover is removed. The two slideably removable plates are particularly advantageous for MRI and CT scanners. The patient typically lies on a bed and the plates are on either side of the body. An operator simply removes each of these two plates and the protective cover is removed.

In another embodiment the protective cover is detached from the ultrasound treatment apparatus when the protective cover is removed. This is advantageous, because many times the patient support for supporting the patient would be operable for moving the patient within the bore of an MRI scanner or CT scanner. Removing the protective plates allows the patient to be moved more easily within a diagnostic apparatus.

In another embodiment the ultrasonic apparatus can also have compartments contained within the patient support. These compartments can be used to hold the protective cover when it is removed from the region. This has the advantage that if the cover is completely contained within the patient support then a patient does not need to be removed from the magnet or from a CT scanner when the protective cover is removed. For the embodiment where the protective cover is comprised of two slideably engaged plates, the operator would typically do a preliminary scan to see if the positioning of the ultrasonic transducer relative to the treatment zone is correct. Then the patient would be removed from the diagnostic region where the operator is able to remove the slideably engaged plates. The embodiment where the compartments are contained within the patient support would allow for an apparatus where the protective cover can be removed when the patient is within a medical imaging device.

In another embodiment the compartments are aligned so that the translational motion of the protective cover is aligned with the length of the patient support. This has the advantage that along the length of the patient support, there is space where the cover can fit. This means that it would be possible to devise a mechanism or system for retracting the covers without having the patient removed from the treatment zone.

In another embodiment the ultrasonic treatment apparatus is further comprised of an actuator which is operable for removing the protective cover from the region. This is an advantage because the operator does not need to manually remove the protective cover, and it can be done automatically when the patient is within a medical scanner. The actuator is adapted for receiving a control signal that signals when the protective cover should be removed from the region and wherein the actuator is further adapted to remove the protective cover from the region upon receiving this control signal. This is an advantage, because a control or computer system can be used for controlling when the protective cover is removed. This allows the removal of the protective cover to be automated.

In another embodiment the ultrasonic treatment apparatus is operable for ablating tissue. This is advantageous because it allows tissue to be treated without invasive surgery. This reduces treatment costs and is less invasive and leads to the patient healing more rapidly.

In another embodiment the ultrasonic treatment apparatus is also operable for treating cancer tumors. This has the advantage also that it is less invasive and does not require surgery. This method also has the advantage that it does not damage the patient's immune system in the way that chemotherapy and radiation therapy can. In another aspect the invention provides for a cartridge which is comprised of an ultrasound coupling and a protective cover. The cartridge is able to be mounted in a receptacle which is adapted for receiving the cartridge in the ultrasonic treatment apparatus. This has the advantage that an operator can simply install a cartridge with an ultrasonic coupling medium into the patient support. The operator will not need to clean the system afterwards, and it leads to a faster workflow. The cover is adapted for being removed when the patient is in place. When the examination is finished, the operator can simply lift the cartridge and the cover out of place, and replace it with a new one.

BRIEF DESCRIPTION OF THE DRAWINGS

In the following preferred embodiments of the invention will be described, by way of example only, and with reference to the drawings in which:

FIG. 1 is a functional schematic showing an embodiment of the invention with a protective cover in place and with the protective cover removed.

DETAILED DESCRIPTION

Figure 2:
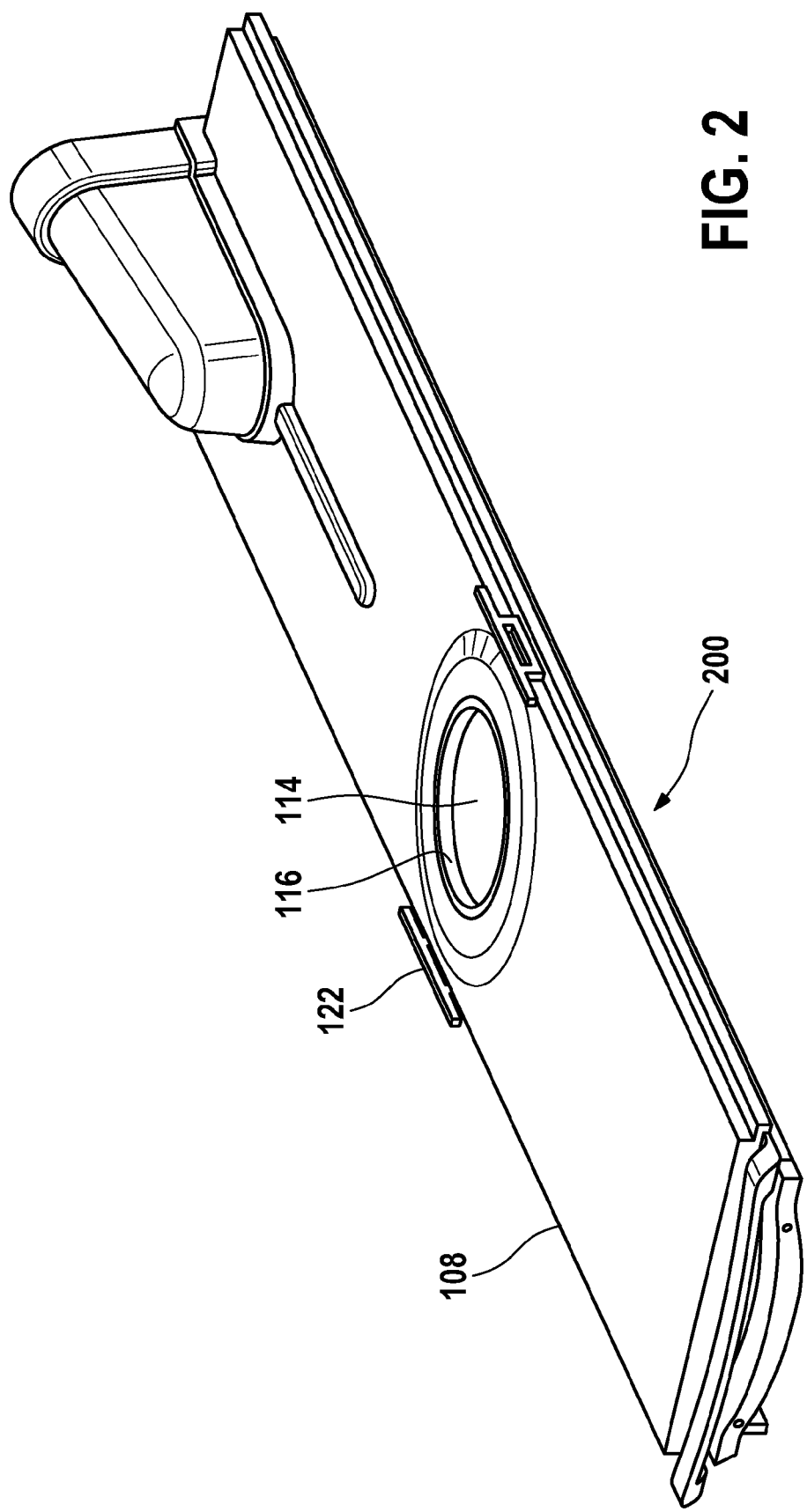
FIG. 2 is a perspective view of an embodiment of the invention with the protective cover removed.

FIG. 1 shows a functional schematic showing an embodiment of the invention with a protective cover in place 100 and with the protective cover removed 102. When the protective cover is in place 100, the patient 106 rests on the patient support 108. The protective cover 104 is positioned over the region 116 that transmits ultrasound. Typically an ultrasonic gel or ultrasonic gel pad is placed within this region 116 to facilitate the transmission of ultrasound. An ultrasound membrane 114 separates the region 116 from the ultrasonic transducer system 110. The ultrasonic transducer system 110 is comprised of an ultrasonic transducer 112, and surrounding the ultrasonic transducer is typically a medium which conducts ultrasound. This can be an ultrasonic gel or it can also be degassed water. The ultrasonic transducer 112 is able to be moved in a limited fashion. This allows the ultrasound to be focused the treatment zone 120 of the body before the treatment starts and allows the adjustment of the treatment zone 120 during treatment. The treatment zone 120 is defined as the region of the body that is treated with the ultrasonic treatment. However, the actuation of the transducer 112 is not unlimited. The patient 106 needs to be positioned properly over the transducer 112.

The protective cover 104 protects the ultrasound membrane 114 and also any ultrasonic conductive material such as a gel pad that may be within the region 116 for transmitting ultrasound. Typically the patient 106 is positioned relative to the patient support 108 so that the ultrasound transducer 112 can properly treat the treatment zone 120. To confirm this, the operator typically puts the patient into a medical imaging zone 134 where medical imaging is performed. If the patient is in the proper position, then the protective cover 104 is removed. However, if the protective cover 104 is able to be removed while the patient is inside the imaging apparatus, then this is straight forward, the protective cover 106 is simply removed. If this is not the case, then the patient is brought out of the imaging device and removed from the medical imaging zone 134. The protective cover 104 is removed and the patient 106 goes back inside of the imaging apparatus. This is particularly the case when an MRI or CT system is used to treat or to guide the treatment process. The patient 106 can easily be repositioned if the position, as checked with the imaging system, is not correct. An advantage is that and ultrasonic conductive material such as a gel pad is not damaged during the repositioning of the patient 106.

102 shows the same embodiment after the operator has removed the protective cover 104 and the patient is inside of a medical imaging zone 134 which is being used to guide the treatment process. Visible is the ultrasound 118 being transmitted from the transducer 112 from the ultrasonic transistor system 110 through the ultrasound membrane 114 and through the region 116 for transmitting ultrasound through the skin and body of the patient 106 to the treatment zone 120. The treatment zone 120 can be adjusted within the patient 106 by moving the transducer 112.

FIG. 2 shows an embodiment of a patient treatment bed for an MRI system 200. The patient support 108, the region for transmitting ultrasound 116 and the ultrasound membrane 114 are visible in this Figure. In this particular embodiment an ultrasonic gel pad would be placed in the region formed by 116 and the patient would lie on the table. Mounting brackets 122 for holding MRI antennas and also for restraining the patient when he or she is being treated are located on either side of the region 116.

Figure 3:
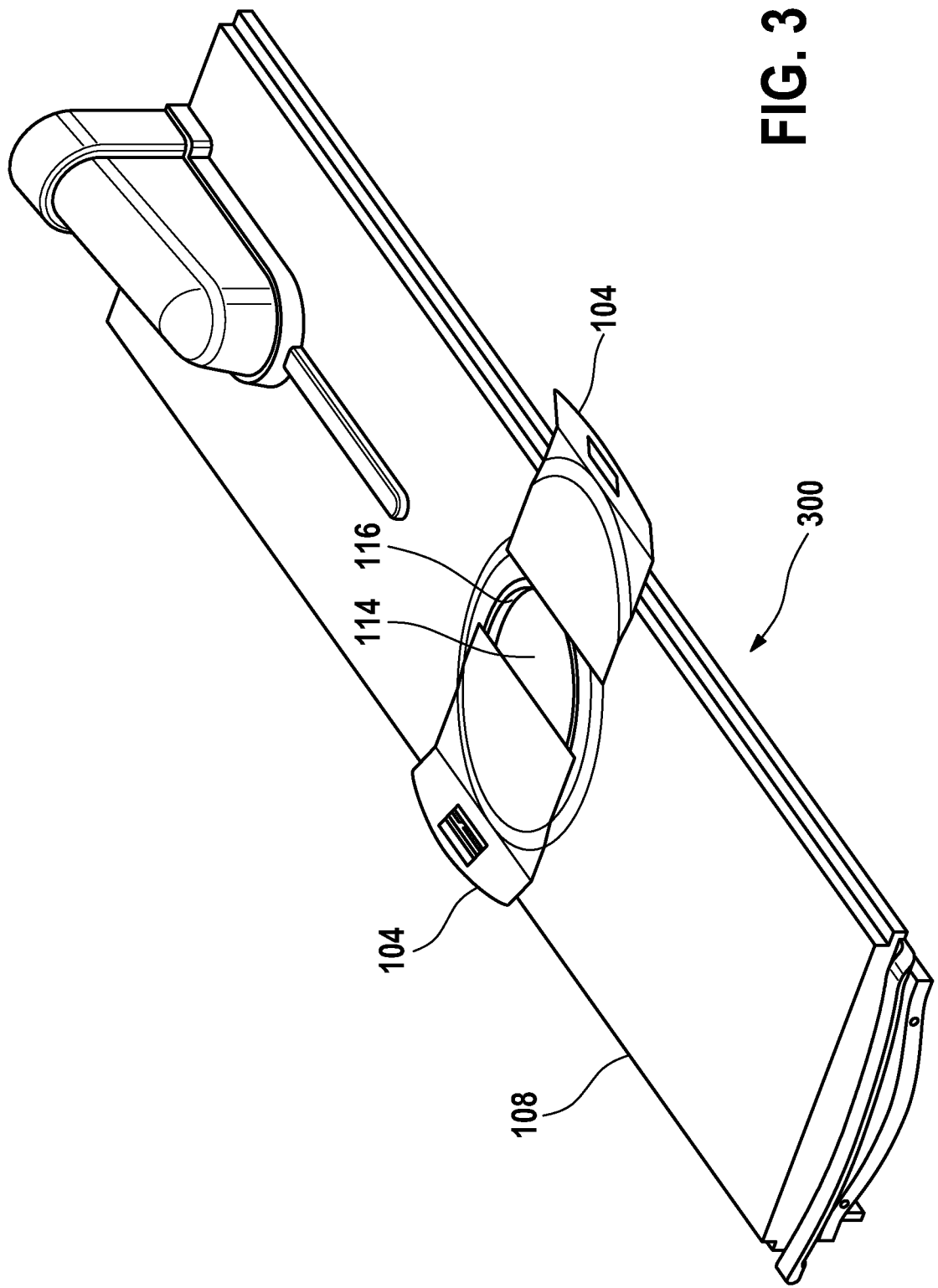
FIG. 3 is a perspective view of an embodiment of the invention that shows the positioning of the protective cover.

FIG. 3 shows the same embodiment of the invention 300 as is shown in FIG. 2. It shows two sliding protective covers 104 in place. One cover covers half of the region 116 for transmitting ultrasound. One cover 104 has been partially removed to illustrate where the split line between the two covers could be. The split line is the position where the two covers meet.

Figure 4:
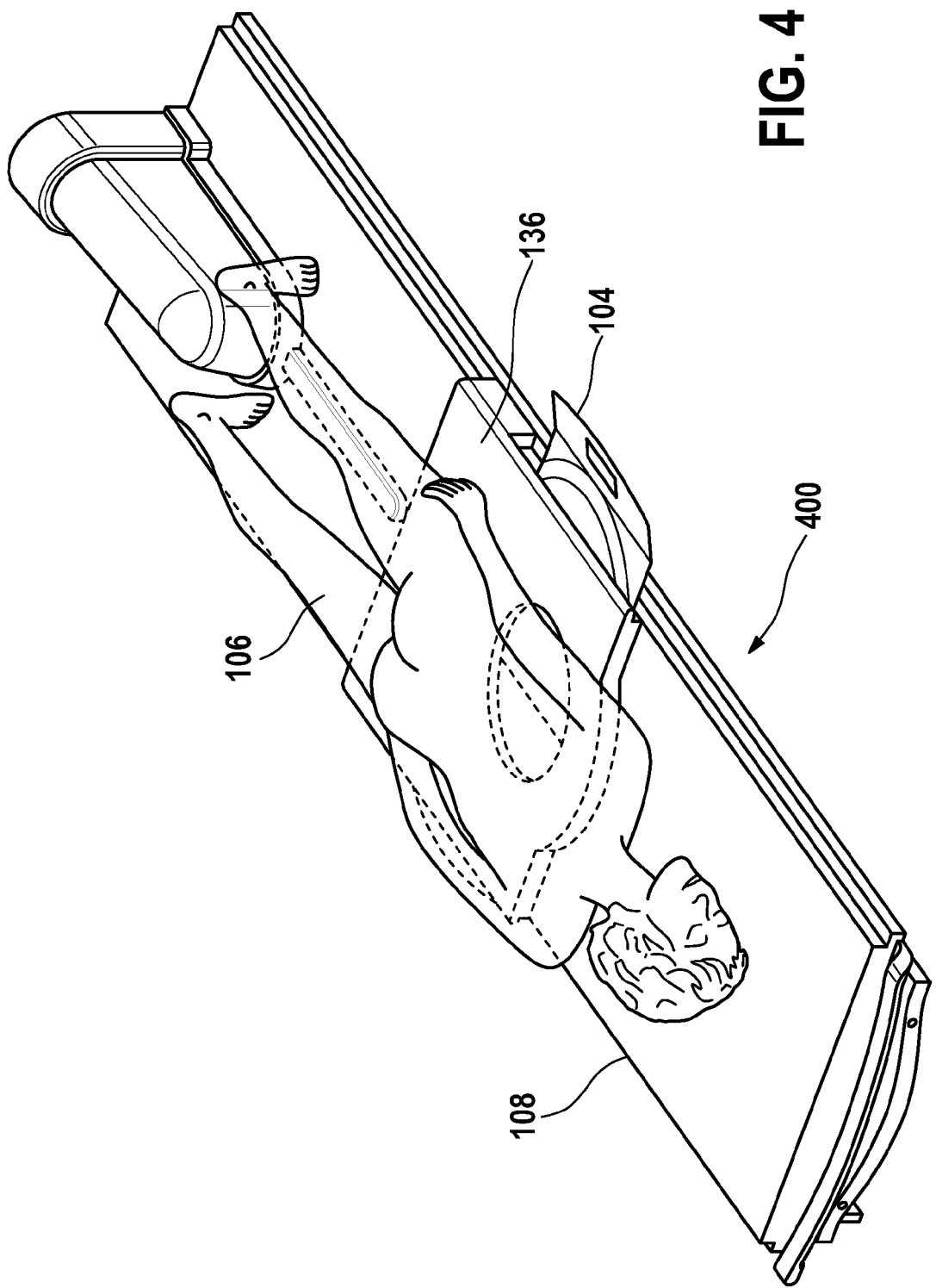
FIG. 4 is a perspective view of an embodiment of the invention showing the positioning of the protective cover and a patient.

FIG. 4 shows the same embodiment of the invention 400 as is shown in FIG. 2. In this Figure a cushion 136 is shown as being on top of the protective covers 104. On top of the cushion and the patient support 108 is a patient. The patient 106 is positioned so that ultrasound is able to enter the body of the patient 106 during treatment.

Figure 5:
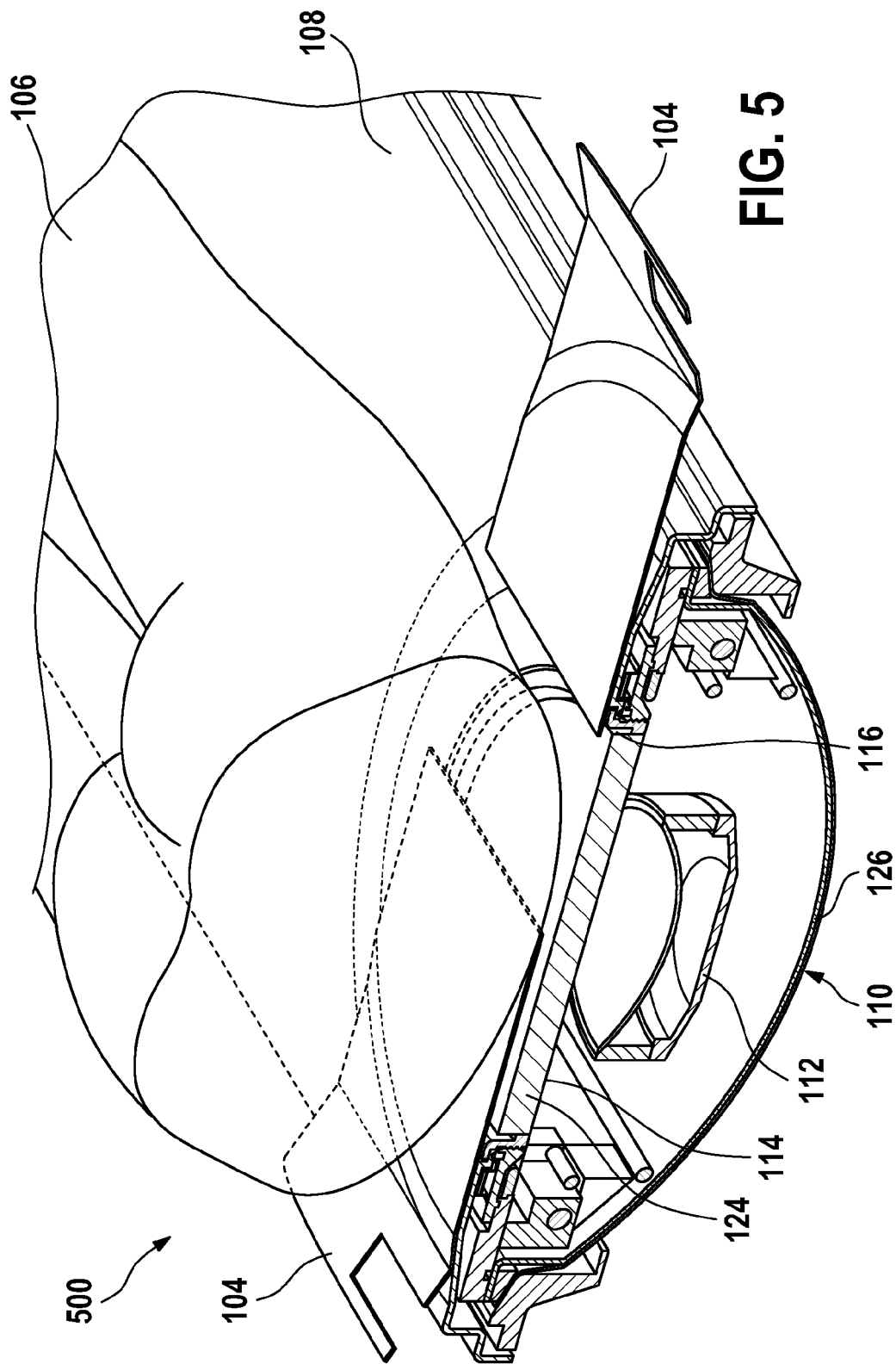
FIG. 5 is a perspective, cross sectional view of an embodiment of the invention.

FIG. 5 shows a perspective cross-sectional view of the same embodiment of the invention 500 as is shown in FIG. 2. This embodiment is comprised of the patient support 108 on top of the patient support are two protective covers 104. The patient rests upon the patient support 108 and the protective covers 104. One protective cover has been partially removed to illustrate the split line between the two covers. Beneath the protective cover is the region for transmitting ultrasound 116. Within the region 116 an ultrasound coupling 124 is visible. In this diagram the ultrasound coupling is a gel pad. Not visible in this Figure is the cushion which is between the patient and the patient support 108 or between the patient and the protective covers 104. Beneath the gel pad is the ultrasound membrane 114. The ultrasound membrane separates 114 the ultrasound coupling 124 from the ultrasound transducer system 110. The ultrasound transducer system 110 is comprised of the water box 126, the ultrasonic transducer 112. The water box contains an ultrasound transmitting medium such as degassed water. Within the ultrasonic transducer system 110 is the ultrasonic transducer 112. This is an ultrasonic transducer and as can be seen in the Figure has a curved shape which is used for focusing ultrasound to a particular point within the body. This ultrasonic transducer 112 can be moved to allow the treatment of different zones within the body during a particular treatment process. The actuators for the ultrasonic transducer are not shown in this Figure.

Figure 6:
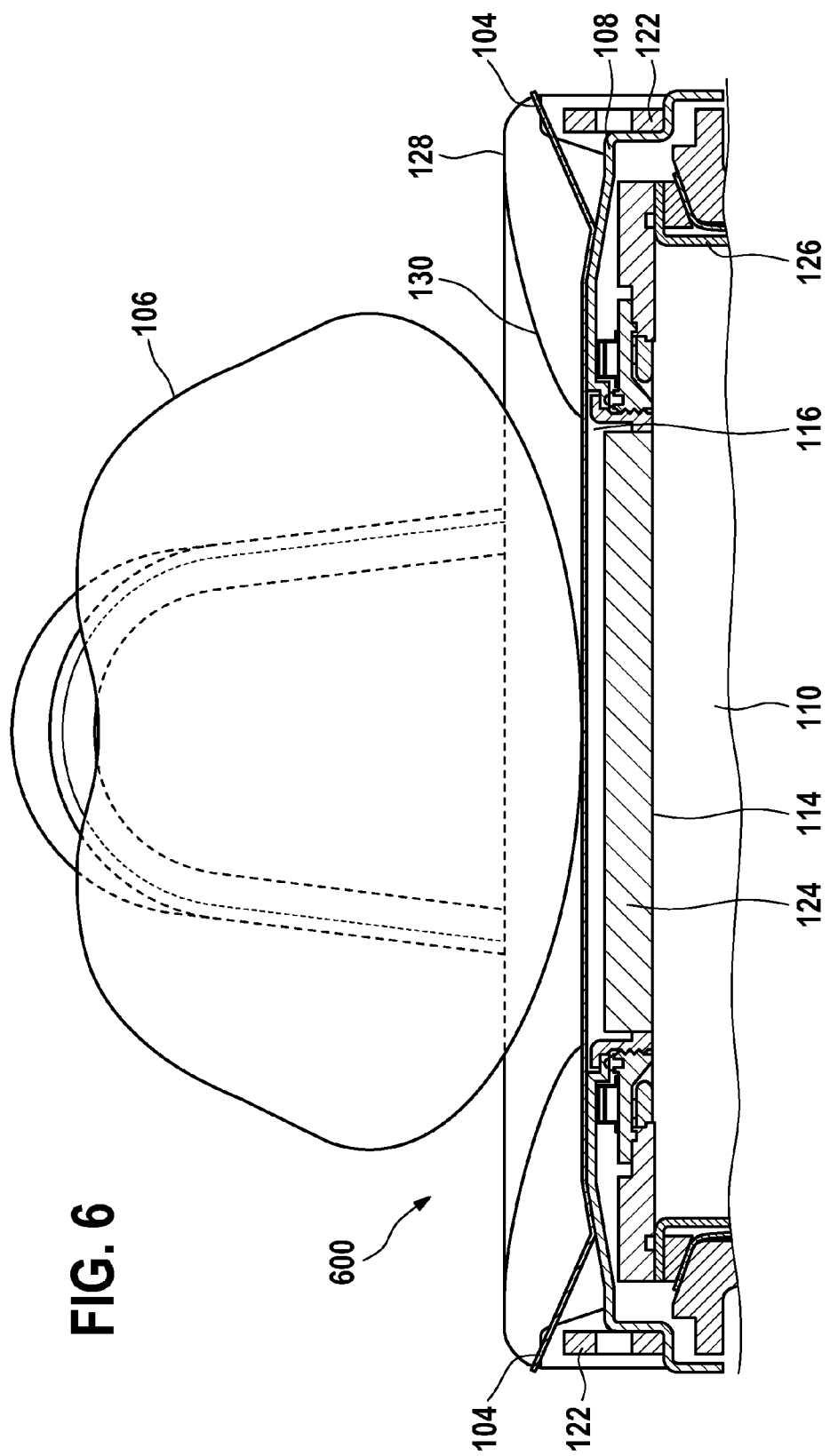
FIG. 6 is a perspective, cross sectional view of an embodiment of the invention.

FIG. 6 shows a perspective cross-sectional view of an embodiment of the same embodiment of the invention 600 as is shown in FIG. 2. This is the same view as FIG. 5, but from a different angle. In this Figure, the patient support 108 is visible. On top of the patient support is a cushion 128 and resting upon the cushion is a patient 106. The patient also rests upon the protective covers 104. The cushion has a sloped surface 130 which is used to partially support the weight of the patient. This sloped surface 130 on the cushion helps to distribute the weight of the patient 106 and reduces the amount of force placed on the protective covers 104. This sloped surface 130 reduces the amount of weight on the protective covers 104, and allows the protective covers 104 to be slid out and removed more easily. The sloped surface 130 also provides a comfortable support for the patient during the examination and aids in properly positioning the patient relative to the ultrasonic transducer system 110. Beneath the protective cover 104, is the region 116 for transmitting ultrasound. This region is protected by the protective cover 104. Inside the region 116 is an ultrasound coupling 124. As in the last Figure, this particular ultrasound coupling is a gel pad. The ultrasound coupling 124 is resting upon an ultrasound membrane 114 which separates the ultrasound coupling 124 from the water box 126 of the ultrasonic transducer system 110. On either side of the region 116 are mounting brackets 122. Again these mounting brackets are used to hold an MRI antenna, and can also be used to restrain the patient. This is an important feature, because a patient restraint aids in forming a proper path for the ultrasound between the patient and ultrasonic transducer system. A patient restraint would hold the patient against and any ultrasonic conductive material such as a gel pad that may be within the region 116.

In FIG. 6, the patient position is checked and is carefully positioned on top of the gel pad. The patient can be asked to tilt to both sides while the protection plates are pulled away. In this way the contact with an ultrasound coupling can be done in a controlled way. Without the protective cover, there is a risk that the gel pad will be destroyed or that air bubbles get in between gel pad or gel pad and mylar window during the positioning of the patient.

Figure 7:
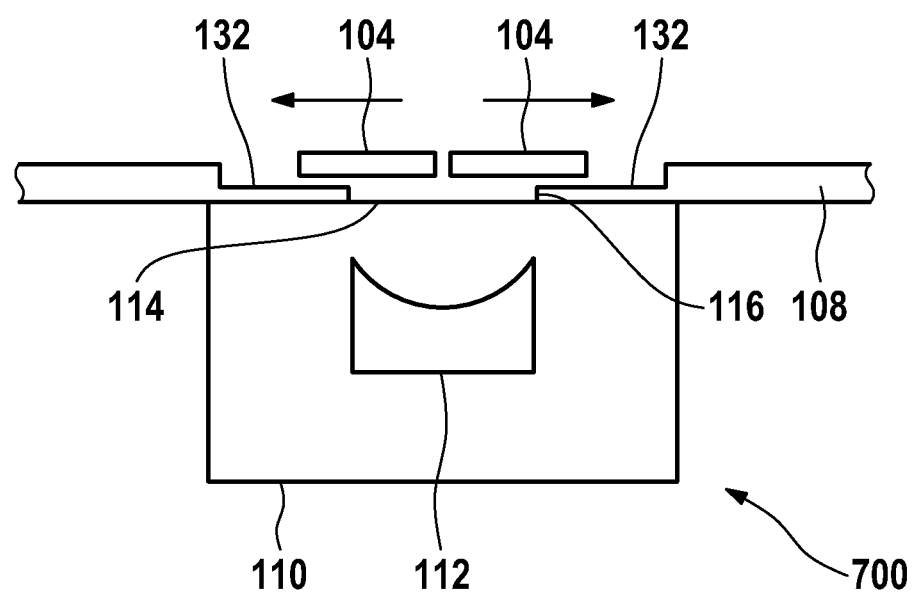
FIG. 7 is a functional schematic showing an embodiment of the invention where the protective cover moves into a compartment when removed.

FIG. 7 shows a functional schematic showing an embodiment of the invention 700 where the protective cover is able to move into a compartment in the patient support 108. In this Figure the patient support 108 is visible. Located within the patient support 108 are compartments 132. These can either be compartments which are able to accept and cover the protective covers 104 or they can simply be depressions in the patient support 108 which the protective covers 104 can move into. Arrows mark the direction of motion that the protective covers 104 take and show how they slide into the compartments 132. Beneath the protective covers 104 is located a region 116 which is for transmitted ultrasound. Between the region 116 is an ultrasound membrane 114 which allows ultrasound to be transmitted from an ultrasonic transducer system 110 to the region 116. The ultrasonic transducer system is mounted beneath the membrane 114. Inside the ultrasonic transducer system 110 is the ultrasonic transducer 112. The ultrasonic transducer as in the other embodiments is used to provide the patient with an ultrasonic treatment 112.

Figure 8:
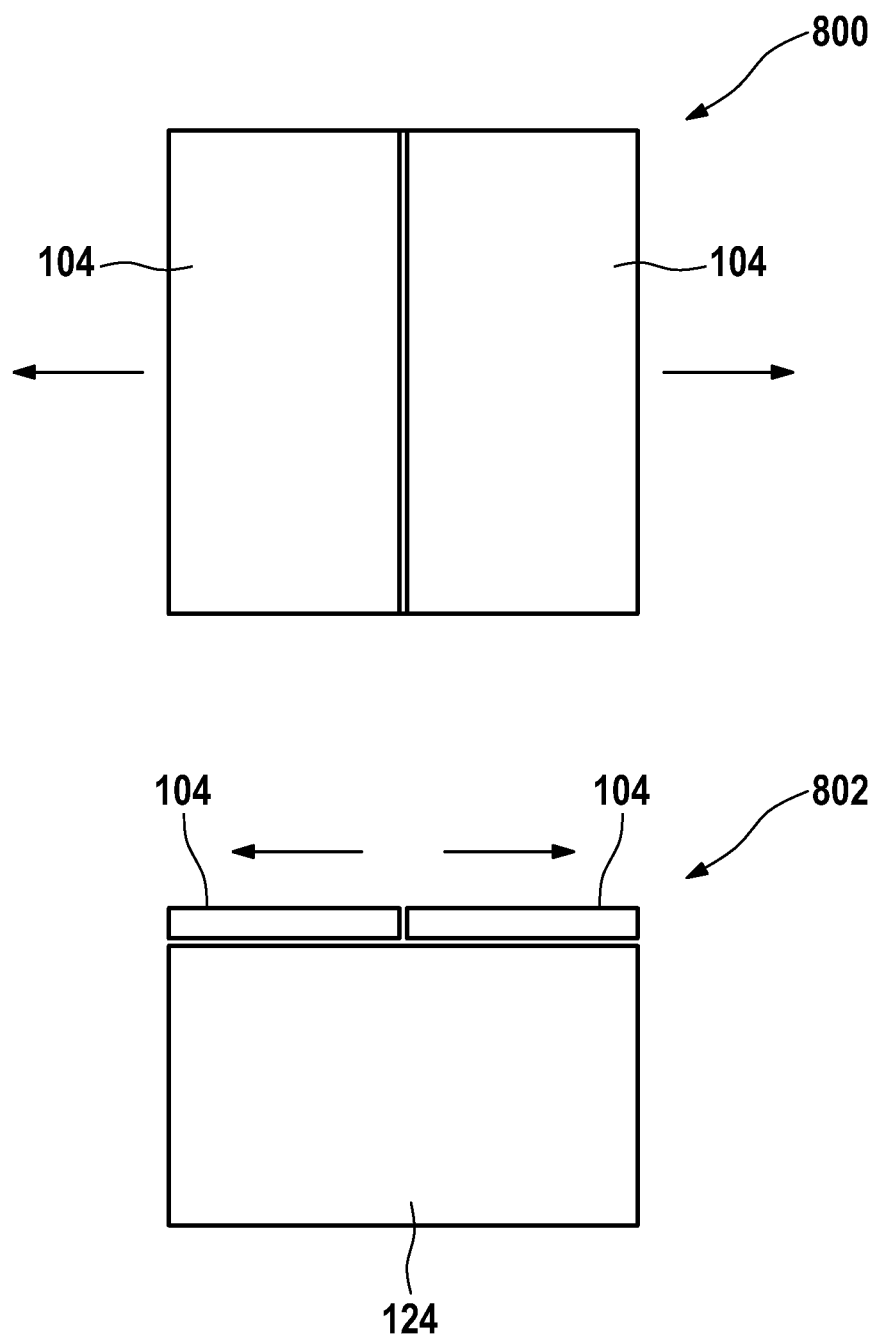
FIG. 8 is a diagram showing an embodiment of a cartridge comprised of a protective cover and an ultrasound coupling.

FIG. 8 is a diagram showing an embodiment of a cartridge 800 comprised of a protective cover 104 and an ultrasonic coupling 124. 800 shows the top view of the cartridge and 802 shows a side view of the cartridge. In this embodiment of the cartridge the cartridge top is covered by two slideable plates which comprise the protective cover 104. Arrows mark how the protective cover would slide away. This cartridge is designed to be placed into a region for transmitting ultrasound 116 such as shown in the embodiment in FIG. 7.

LIST OF REFERENCE NUMERALS

| | |
|---|---|
| 100 | Embodiment of an ultrasonic treatment apparatus with the protective cover installed |
| 102 | Embodiment of an ultrasonic treatment apparatus with the protective cover removed |
| 104 | Protective cover |
| 106 | Patient |
| 108 | Patient support |
| 110 | Ultrasonic transducer system |
| 112 | Ultrasonic transducer |
| 114 | Ultrasound membrane |
| 116 | Region (for transmitting ultrasound) |
| 118 | Ultrasound waves |
| 120 | Treatment zone |
| 122 | Mounting bracket |
| 124 | Ultrasound coupling |
| 126 | Waterbox |
| 128 | Cushion |
| 130 | Sloped surface |
| 132 | Compartment |
| 134 | Medical imaging zone |
| 200 | Embodiment of an ultrasonic treatment apparatus |
| 300 | Embodiment of an ultrasonic treatment apparatus |
| 400 | Embodiment of an ultrasonic treatment apparatus |
| 500 | Embodiment of an ultrasonic treatment apparatus |
| 600 | Embodiment of an ultrasonic treatment apparatus |
| 700 | Top view of cartridge |
| 800 | Top view of cartridge |
| 802 | Side view of cartridge |

The invention claimed is:

1. An ultrasonic treatment apparatus comprising:
   a support surface configured to support a patient, the support surface including a treatment zone;
   an ultrasound transducer configured for ultrasonic treatment;
   a membrane formed in the support surface, the membrane configured and positioned to transmit ultrasound from the ultrasound transducer to the treatment zone; and
   a protective cover configured and positioned to cover and protect the membrane, the protective cover is removable from the membrane while the patient is positioned relative to the treatment zone to receive treatment from the ultrasound transducer.

2. The ultrasonic treatment apparatus of claim 1, wherein the support surface surrounds the membrane, and wherein the support surface slopes towards the treatment zone.

3. The ultrasonic treatment apparatus of claim 1 further comprising a medical imaging device selected from one of an MRI scanner, a CT scanner, and an ultrasound imaging system.

4. The ultrasonic treatment apparatus of claim 3, wherein the support surface is operable for positioning the patient relative to the medical imaging device.

5. The ultrasonic treatment apparatus of claim 1, comprising an ultrasound coupling configured to transmit ultrasound from the ultrasound membrane to the patient.

6. The ultrasonic treatment apparatus of claim 1, wherein the protective cover is slideably engaged.

7. The ultrasonic treatment apparatus of claim 1, wherein the protective cover is comprised of two slideably engaged plates.

8. The ultrasonic treatment apparatus of claim 1, wherein the protective cover is detached from the ultrasonic treatment apparatus when the protective cover is removed from the membrane.

9. The ultrasonic treatment apparatus of claim 6, further comprising one or more compartments included within the support surface for holding the protective cover when it is removed from the membrane.

10. The ultrasonic treatment apparatus of claim 9, wherein the one or more compartments are aligned so that the translational motion of the protective cover is aligned with the length of the support surface.

11. The ultrasonic treatment apparatus of claim 1, further comprising an actuator configured to remove the protective cover from the membrane, to receive a control signal for indicating when the protective cover should be removed from the membrane, and to remove the protective cover from the membrane upon receipt of the control signal.

12. The ultrasonic treatment apparatus of claim 1, wherein the ultrasound transducer is configured to ablate tissue.

13. The ultrasonic treatment apparatus of claim 1, wherein the ultrasound transducer configured to treat cancer tumors.

14. The ultrasonic treatment apparatus of claim 1, wherein the cartridge comprises an ultrasound coupling.

15. An ultrasonic treatment apparatus comprising:
   a cartridge including a protective cover;
   a support surface configured to support a patient, the support surface including a treatment zone and a receptacle configured to mount the cartridge;
   an ultrasound transducer configured for ultrasonic treatment;
   a membrane formed in the support surface and configured to transmit ultrasound from the ultrasound transducer to the treatment zone; and
   wherein the protective cover configured to be removed from the membrane while the patient is positioned relative to the treatment zone to receive treatment from the ultrasound transducer.

16. An ultrasonic treatment apparatus comprising:
   a support surface configured to support a patient, the support surface including a treatment zone;

an ultrasound transducer configured for ultrasonic treatment;
a membrane formed in the support surface, the membrane configured and positioned to transmit ultrasound from the ultrasound transducer to the treatment zone;
a protective cover configured and positioned to cover and protect the membrane, the protective cover is removable from the membrane while the patient is positioned relative to the treatment zone to receive treatment from the ultrasound transducer; and
an actuator configured to remove the protective cover from the membrane, to receive a control signal for indicating when the protective cover should be removed from the membrane, and to remove the protective cover from the membrane upon receipt of the control signal.

* * * * *